US008083926B2

(12) United States Patent
Chen

(10) Patent No.: US 8,083,926 B2
(45) Date of Patent: Dec. 27, 2011

(54) NANOPORE STRUCTURED ELECTROCHEMICAL BIOSENSORS

(76) Inventor: Ellen T. Chen, Germantown, MD (US)

(*) Notice: Subject to any disclaimer, the term of this patent is extended or adjusted under 35 U.S.C. 154(b) by 442 days.

(21) Appl. No.: 11/785,660

(22) Filed: Apr. 19, 2007

(65) Prior Publication Data
US 2008/0237063 A1 Oct. 2, 2008

Related U.S. Application Data

(60) Provisional application No. 60/792,902, filed on Apr. 19, 2006.

(51) Int. Cl.
*G01N 27/327* (2006.01)
(52) U.S. Cl. ............... 205/792; 204/403.01; 977/920
(58) Field of Classification Search .. 204/403.1–403.15; 205/775–794.5; 435/180, 4–40.52; 422/68.1–98; 436/62–71, 500–548; 977/920–922, 957–959
See application file for complete search history.

(56) References Cited

U.S. PATENT DOCUMENTS

| | | | | |
|---|---|---|---|---|
| 6,582,583 B1* | 6/2003 | Chen | ............ | 205/317 |
| 6,632,748 B2* | 10/2003 | Yim et al. | ............ | 438/780 |
| 6,855,556 B2* | 2/2005 | Amiss et al. | ............ | 436/95 |
| 7,063,753 B1* | 6/2006 | Chen et al. | ............ | 148/108 |
| 2003/0064095 A1* | 4/2003 | Martin et al. | ............ | 424/451 |
| 2004/0072158 A1* | 4/2004 | Henkens et al. | ............ | 435/6 |
| 2004/0236244 A1* | 11/2004 | Allen et al. | ............ | 600/532 |

OTHER PUBLICATIONS

Songqin Liu et al., *Biosensors and Bioelectronics*, 19:177-183 (2003).
Woochang Lee et al., *Biosensors and Bioelectronics*, 19:185-192 (2003).
Songqin Liu et al., *Biosensors and Bioelectronics*, 19:963-969 (2004).
Bilal El-Zahab et al., *Biotechnology and Bioengineering*, 87(2):178-183 (Jul. 2004).
S. J. Updike et al., *Nature*, 214:986-988 (Jun. 1997).
H. Burkhard Dick et al., *Ophthalmic Research*, 33:61-67 (2001).
Hagan Bayley et al., *Molecular Membrane Biology*, 21:209-220 (Jul.-Aug. 2004).
Rajeev Prabhakar et al., *Biochimica et Biophysica Acta*, 1647:173-178 (2003).
Yang Tian et al., *Analytical Chemistry*, 74(10):2428-2434 (2002).
Joseph Wang, *Analyst*, 130:421-426 (2005).
Hagan Bayley et al., *Nature*, 413:226-229 (Sep. 2001).
Zong Dai et al., *Anal. Chem.*, 75:5429-5434 (2003).

* cited by examiner

*Primary Examiner* — Kaj K Olsen
*Assistant Examiner* — Susan Thai

(57) ABSTRACT

The present invention provides a novel biosensor and measuring method. The novel biosensor of the present invention comprises an electrode having a nanopore structured and catalytically active cyclodextrin attached thereto. The biosensor of the present invention has demonstrated robust analytical performance for direct glucose measurement without mediators or without using native enzyme, which is especially beneficial in the hypoglycemia range.

24 Claims, 18 Drawing Sheets

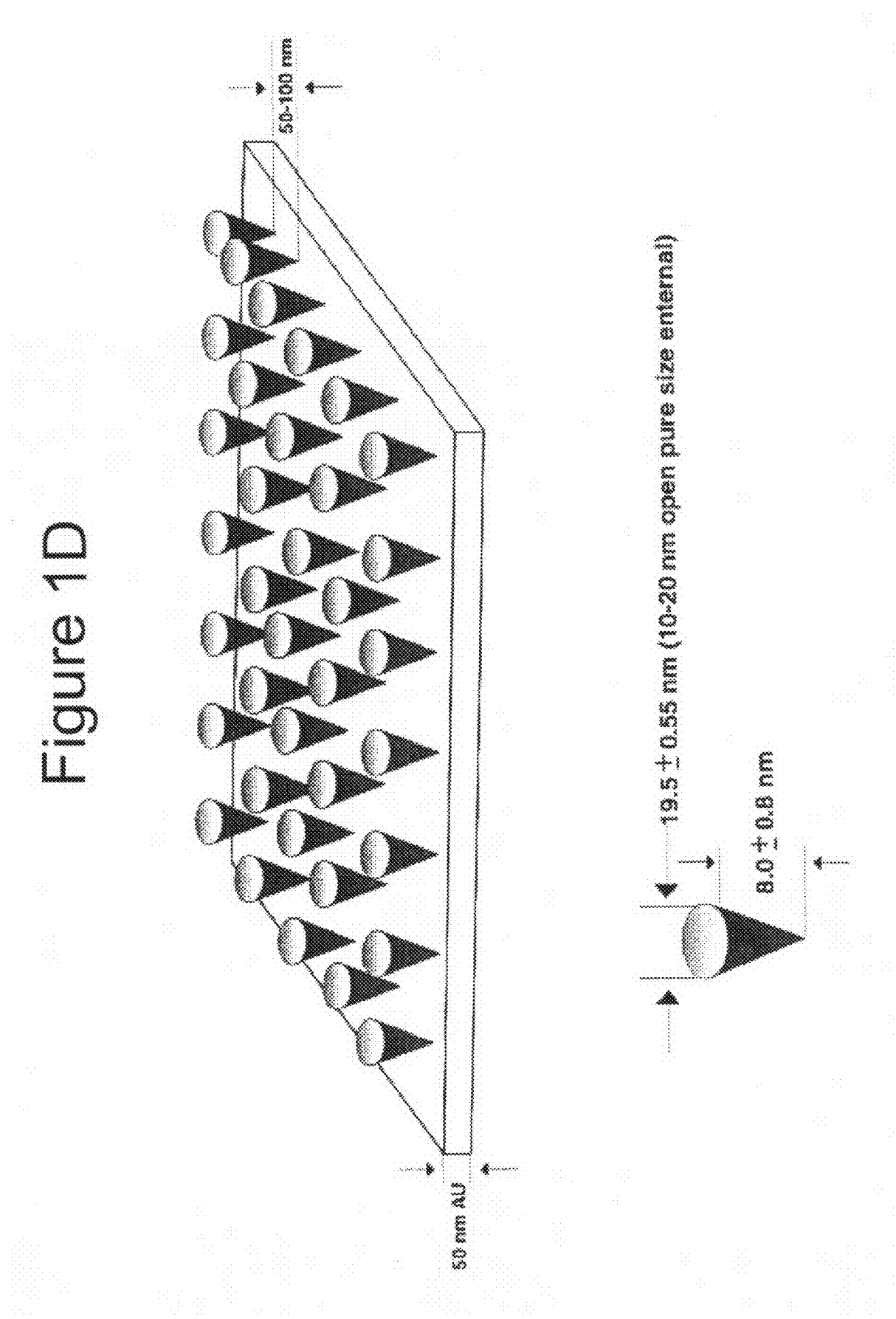

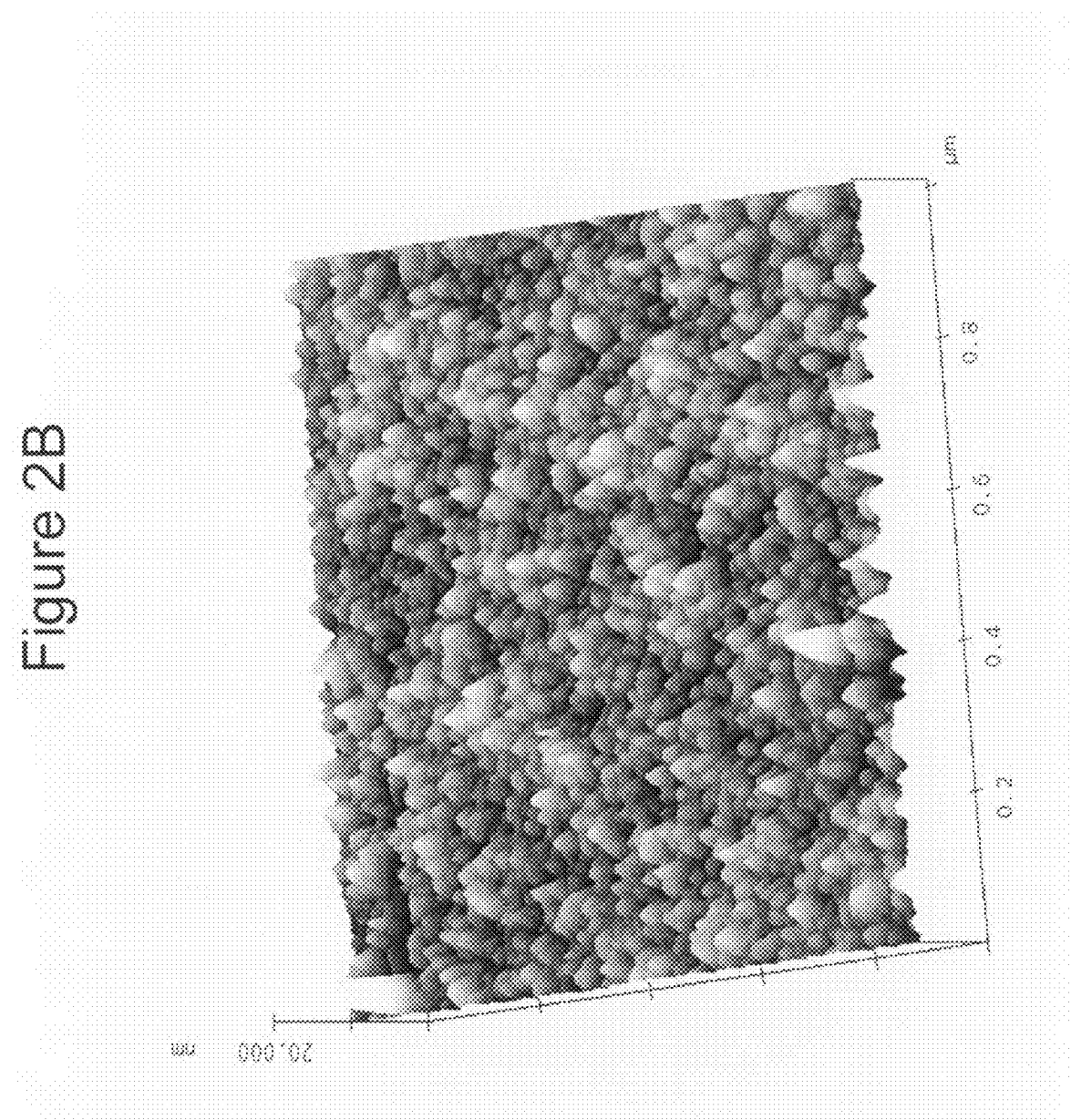

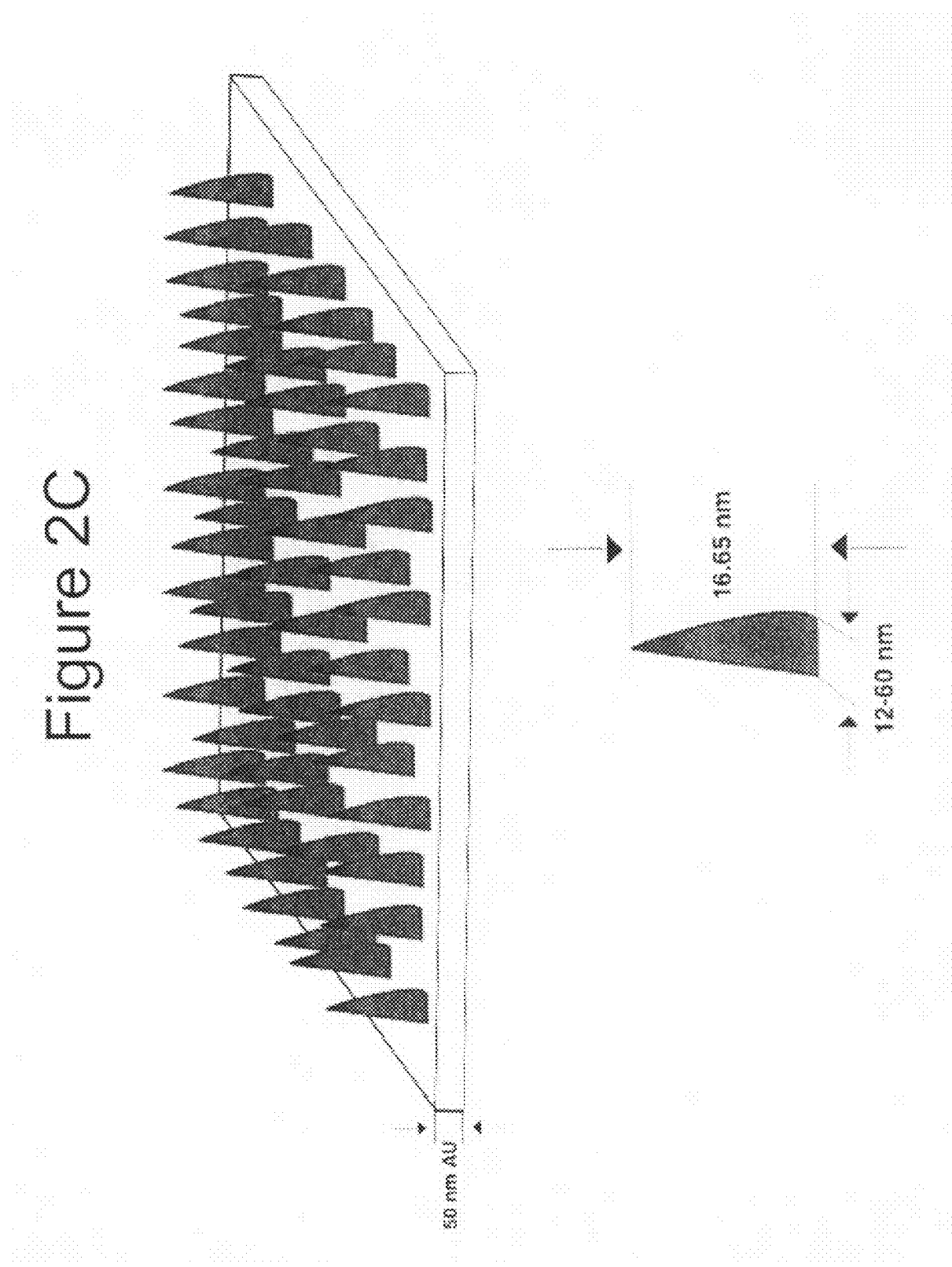

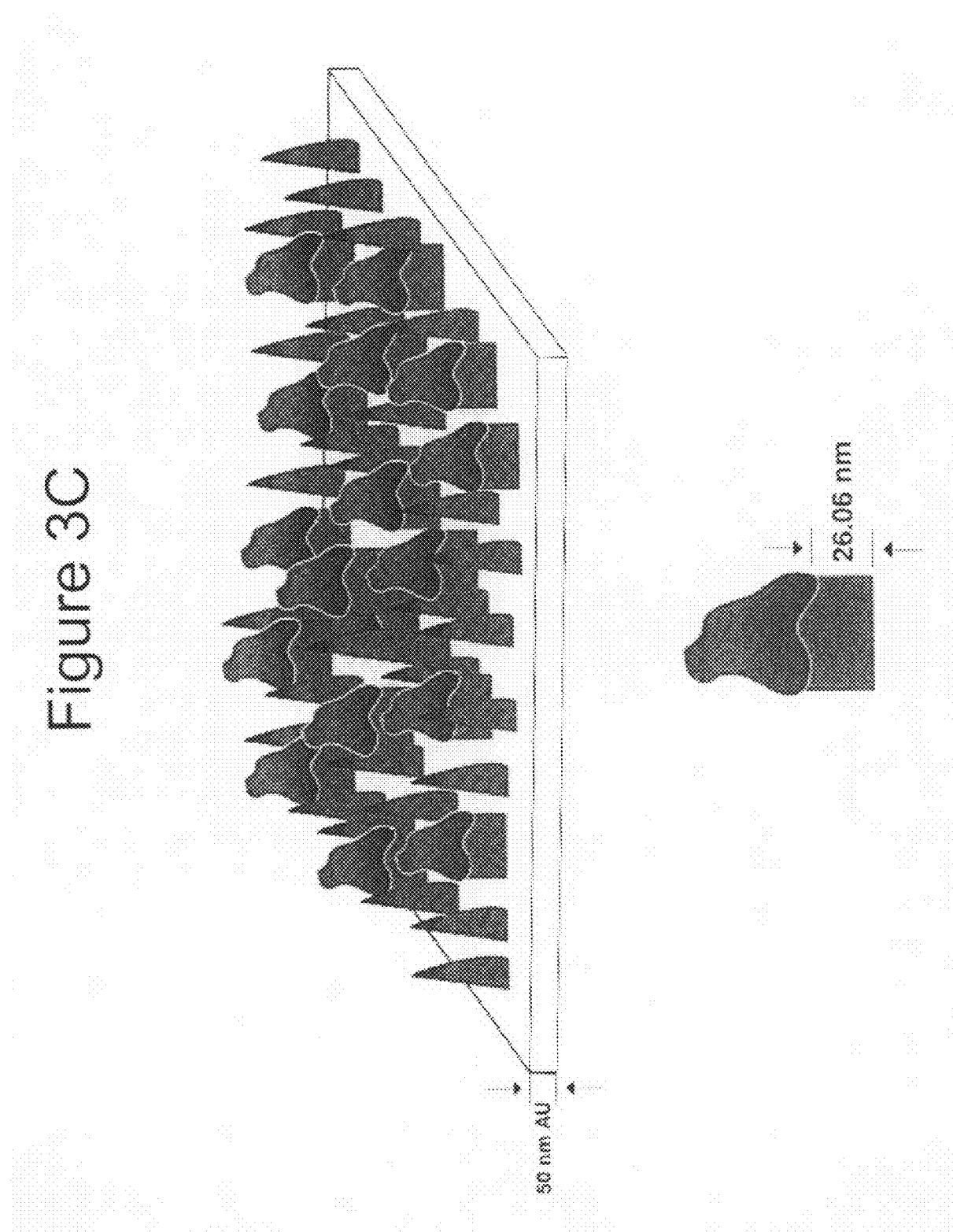

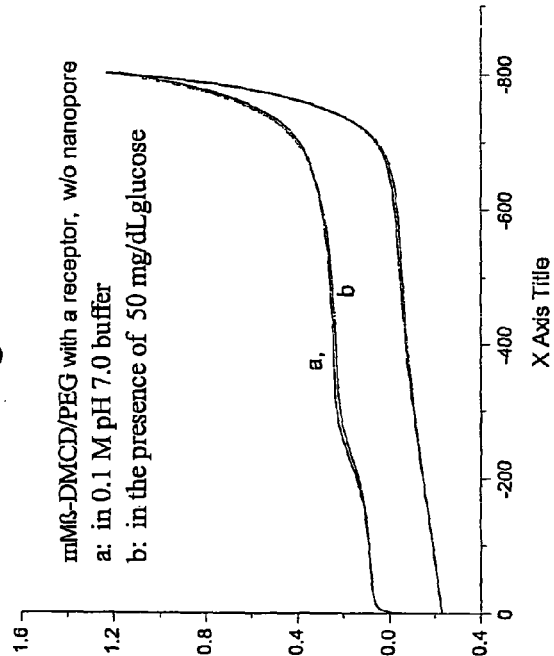
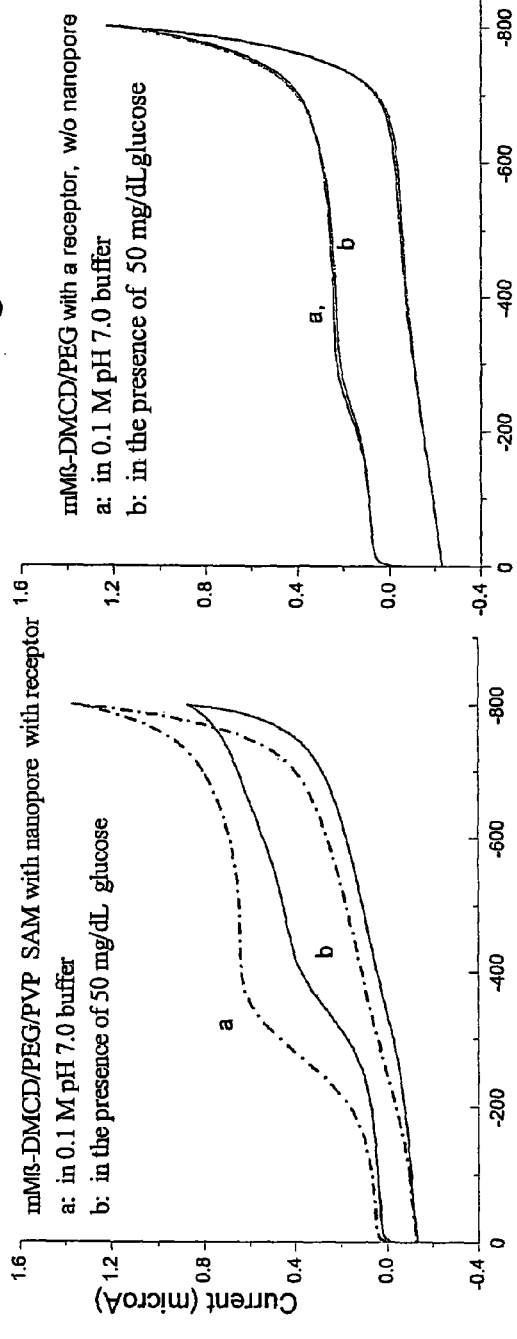
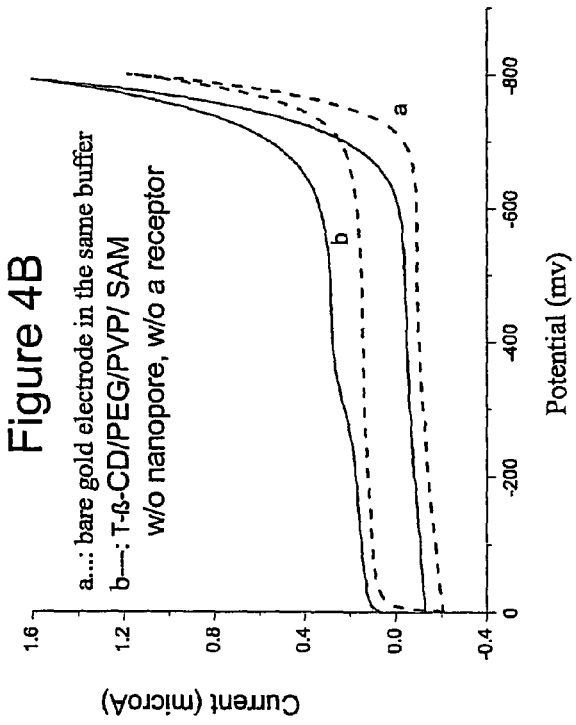

Figure 11
mM-β-DMCD
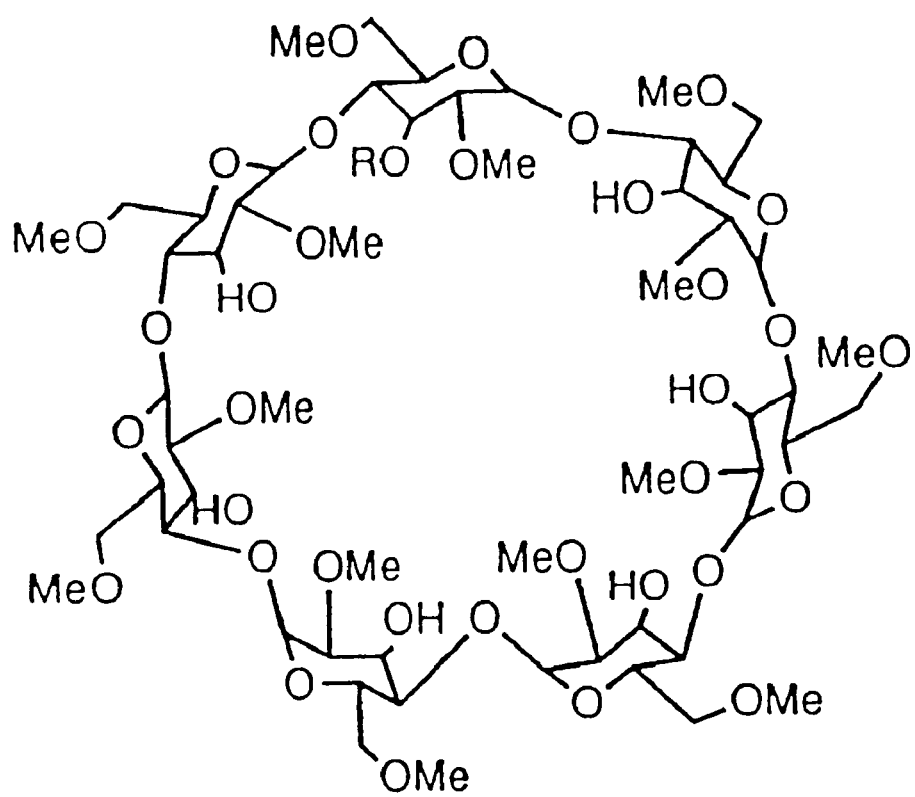
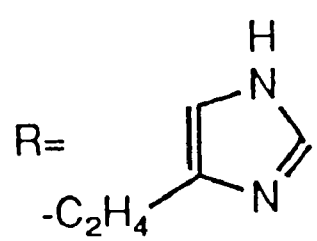

NANOPORE STRUCTURED ELECTROCHEMICAL BIOSENSORS

CROSS-REFERENCE TO RELATED APPLICATIONS

This patent application claims the benefit of U.S. Provisional Patent Application Ser. No. 60/792,902 filed Apr. 19, 2006. The entire disclosure of the prior Patent Application Ser. No. 60/792,902 is hereby incorporated by reference, as is set forth herein in its entirety.

STATEMENT REGARDING FEDERAL FUNDED RESEARCH

This invention was made with governmental support through the U.S. Department of health and Human Services, U.S. Food and Drug Administration. The United States Government has certain rights in this invention.

FIELD OF THE INVENTION

The present invention relates to the field of biosensors and, in particular, to biosensors comprising a catalytically active cyclodextrin in a nanopore form.

BACKGROUND OF THE INVENTION

Monitoring blood glucose levels regularly is very important in proper diabetes management, especially for children with type I diabetes. The conventional glucose sensor technologies have limited the development of glucose sensors, especially in its measurements of blood glucose in the hypoglycemia range (see reference 23). The third generation glucose sensors based on DET phenomena were widely reported (see references 6-8). The third generation biosensors for direct glucose measurements are based on an intriguing phenomenon known for the last decade as the bioelectrocatalysis with the direct electron transfer (DET) between the electrode and the redox active sites of bio molecules (see references 1-5). Direct measurement of analyte without using mediators is one the advantages that this type of sensors offer, because the mediators are leachable from the polymer network and are toxic.

Nano-structured material used for developing novel sensors have been reported in the last decade. Colloidal nano gold particles have been extensively studied for the utility of promoting DET between enzymes and the nano particles (see references 9-10). Joseph Wang had extensive review articles in this field (see references 11-12). The carbon nanotube modified glucose oxidase (GOD) enzyme electrode capable of promoting electron transfer is reviewed in his articles. Vaseashta and Irudayaraj have a review paper on nanostructured sensors (see reference 13).

Nanowire and nanopore based sensors have drawn great interest recently because they are extremely sensitive and well suited for multiple target detection, which overcame the disadvantages of previous technology. However, as the reviewers Vaseashta and Irudayaraj point out, the technology is still in the development stage and the robustness has not been established (see reference 13). It has been shown that the nanopores played an important role in enabling multiple step reactions with higher reaction rate in comparison with the same system immobilized on polystyrene without nanopores (see reference 14).

Cylcodextrins (CD) existing in nature consists of 6 to 12 glucose units. The shapes of cyclodextrins are like donuts, or a truncated conical basket. These CDs have an internal hydrophobic property and external hydrophilic property. The internal pore diameter is 0.78 nm for β-CD, and its height is 0.78 nm. In the reports on recent development in this field, biosensors were developed utilizing the unique properties of CDs to form nanopores or nanotubes with polymers and biological materials (see references 17-22) to detect various toxic substances which are undetectable by conventional sensors.

As indicated above, however, robust nanopore structured sensors have yet to be reported. Therefore, there is a need for a biosensor for accurate glucose measurement, especially in the hypoglycemia range. In addition, there is a need for biosensors that do not utilize a mediator. These and other needs have been met by the present invention.

SUMMARY OF THE INVENTION

It is an object of the present invention to provide a sensor comprising an electrode and a cyclodextrin in the form of a nanopore and chemically modified to be electrocatalytically active affixed to said electrode. The nanopore structured self-assembling membrane (SAM) sensors can be used for direct measurement of analyte without using the polymer network's leachable and potentially toxic mediators.

It is also an object of the present invention to provide a new generation of electrochemical glucose biosensor that is based on a nanopore structured cyclodetrin SAM and a biomimetic Histidine residue (His 516) receptor of glucose oxidase that is located inside of the CD cavity. The biosensor of the present invention has demonstrated robust analytical performance for direct glucose measurements, especially in the hypoglycemia range.

It is a further object of the present invention to provide a method for detecting or measuring a material, such as glucose, in a sample comprising the step of contacting the sample with a biosensor wherein the biosensor comprises a nanopore structured and chemically modified cyclodextrin.

It is a still further object of the present invention to provide a method for constructing a biosensor comprising the step of contacting an electrode with a solution comprising chemically modified cyclodextrin to form a nanopore structure. In preferred embodiments, the cyclodextrin may be mM-β-DMCD (mono-modified β-dimethylcyclodextrin) and it forms self-assembling membrane together with PEG (polyethylene glycol) and PVP (poly(4-vinylpyridine)).

BRIEF DESCRIPTION OF THE DRAWINGS

FIG. 1D illustrates that mM-β-DMCD/PEG/PVP with nanopore structure forms conductive polymer blocks.

FIGS. 2A and 2B show AFM 3D images of mM-β-DMCD/PEG without nanopore structure, respectively.

FIG. 2C illustrates mM-β-DMCD/PEG with nanopillar structure.

FIG. 3C illustrates T-β-CD/PEG/PVP cross-linking CD copolymer.

FIG. 4A shows the current vs. voltage Cyclic Voltammetry (CV) curves of a: the mM-β-DMCD/PEG/PVP SAM electrode with nanopore in 0.1 M pH 7.0 buffer; b: the same sensor in the presence of 50 mg/dL glucose at scan rate 50 mv/s.

FIG. 4B shows CV curves of a: bare gold electrode without glucose, b: the T-β-CD/PEG/PVP CD copolymer electrode without glucose in the 0.1 M pH 7.0 buffer under same experimental conditions.

FIG. 4C shows CV curves of a: mM-β-DMCD/PEG SAM electrode without glucose, b: with 50 mg/dL glucose.

FIG. 11 is a representation of the structure of a catalytically active cyclodextrin.

DETAILED DESCRIPTION OF THE INVENTION

Example 1

Constructing the Biosensor

Figure 1A:
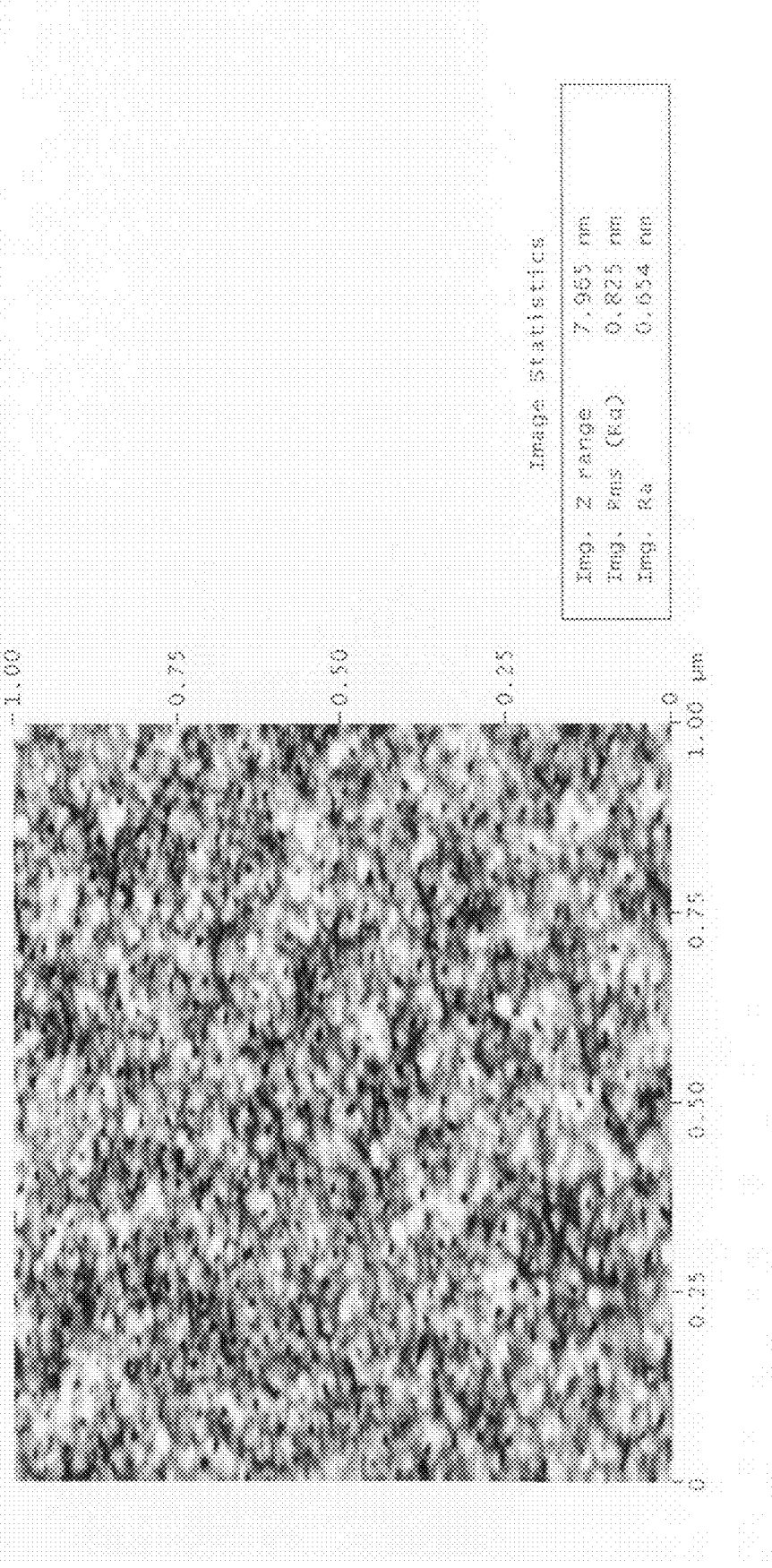
FIG. 1A shows two-dimensional atomic force microscopy (AFM) image of nanopore structured mM-β-DMCD/PEG/PVP SAM with an internal receptor imidazolyle. Brighter areas represent higher topography. The roughness measurements Peak-to-Valley (Z range), Root Mean Square (RMS), and Average Roughness ($R_a$) are also shown for this image.

Reagent grade poly (4-vinylpyridine) (PVP), polyethylene glycol diglycidyl ether (PEG), triacetyl-β-CD (T-β-CD), β-CD/epichlorohydrin, β-D-glucose were purchased from Aldrich-Sigma. The PVP was recrystallized in methanol. The biomimetic glucose enzyme, which is a biomimetic Histidine residue (His-516) receptor of glucose oxidase and mimics the active center of native glucose enzyme, named mM-β-DMCD was synthesized generally according to the published procedures (E. T. Chen and H. L. Pardue, *Analytical applications of catalytic properties of modified-cyclodextrins*. Anal. Chem. 65, 2563-2567, 1993, which is hereby incorporated by reference in its entirety as if set forth herein). U.S. Pat. No. 6,582,583 issued on Jun. 24, 2003 is also hereby incorporated by reference in its entirety as if set forth herein. Briefly, β-DMCD may be reacted first with sodium hydride in dry tetrahydrofuran under a nitrogen atmosphere at 35-38° C. for 10 hours. The solution is then cooled to 0° C. and mixed with a solution of 2-(4-imidazolyl)-ethyl bromide in tetrahydrofuran and heated to 25° C. for 10 hours to produce the mM-β-DMCD. The structure of the mM-β-DMCD is shown in FIG. 11.

A gold electrode (1.6 mm diameter) polished successively with 0.1 and 0.05 μm alumina slurry (BAS), then washed with double distillation water, then sonicated with methanol, then with water. After that, the electrode was polished with diamond solution (BAS), and washed with double distillation water and sonicated in methanol, then with double distillation water. Dry $N_2$ was used to dry the electrode, and then the gold electrode was put in a 35° C. incubator for further drying for 1 hour before use. The gold electrode with a SAM film was used as the working electrode. The platinum wire electrode was the auxiliary electrode and the Ag/AgCl electrode was the reference electrode.

A class 100 level of a clean room was used for all SAM developments. A mixture of PVP/PEG/mM-β-DMCD (see E. T. Chen. *Amperometric biomimetic enzyme sensors based on modified cyclodextrin as electrocatalysts*, and U.S. Pat. No. 6,582,583 issued on Jun. 24, 2003, both of which are hereby incorporated by reference in entirety as if set forth herein) solution (e.g. 4 μL) was dropped using a syringe by 2×4 μL onto the gold electrode surface at a room temperature and the fabricated SAM electrode was immediately sealed in a $N_2$ filled container and incubated for 48 hours at 35.0° C., then the electrode was washed with double distilled water to remove unbounded chemicals, then was incubated for 2 hours before use. The same protocols were used for fabrication of the PEG/mM-β-DMCD SAM film without PVP; and a T-β-CD/PEG/PVP/β-C copolymer SAM sensor was also fabricated under the same procedures. The differences in the composition and concentration between the U.S. Pat. No. 6,582,583 and an embodiment of the present invention is shown below:

TABLE 1

Comparison of the composition and concentration of the PVP/PEG/mM-β-DMCD mixture

| | Composition (v/v) | | | Concentration (mg/mL) | | |
|---|---|---|---|---|---|---|
| | PVP | PEG | mM-β-DMCD | PVP | PEG | mM-β-DMCD |
| U.S. Pat. No. 6,582,583 | 5 | 2 | 10 | 4 | 2 | 4.0 |
| The embodiment of the present invention | 3 | 1 | 6 | 0.4 | 2 | 4.2 |

It should be noted that different factors have impacts on the formation of different nanostructured SAM film on a gold surface. A comparison of these factors in an embodiment of the present invention and U.S. Pat. No. 6,582,583 is shown below:

TABLE 2

Comparison of the structure of the gold film

| | the gold film | Film thickness |
|---|---|---|
| U.S. Pat. No. 6,582,583 | Single crystal AU(1, 1, 1) | 10 nm |
| The embodiment of the present invention | The purity >99.99% | 50 nm |

A single crystal gold 1×1×1 film that causes phase structure transition was reported in Y. Kondo et al. (see reference 28). The different thickness of the gold film has an impact on the formation of the SAM film on the gold surface.

TABLE 3

Comparison of the processing procedure

| | Cleaning procedure on the gold surface | Fabrication procedure |
|---|---|---|
| U.S. Pat. No. 6,582,583 | Ultra sonic plasma cleaning procedure was used. | To form the nanotube in FIG. 4 of the U.S. Pat. No. 6,582,583, the gold planer electrode was completely immersed into a solution consisting of PVP/PEG/mM-β-DMCD(5:2:10 (v/v)) in a sealed container for 24 hours at a room temperature, then the gold electrode was taken out and incubated for 48 hours at 37° C. and cleaned with distilled water for 10 minutes, then dried for 2 hours at 37° C. to allow the formation of the nanotube by self-assembly. |
| The embodiment of the present invention | No cleaning procedure was applied onto the gold surface. | To form the nanopore structure shown in FIGS. 1A, 1B and 1C, a drop (4 μL) of solution consisting of PVP/PEG/mM-β-DMCD was applied onto the gold chip surface at a room temperature and immediately incubated for 48 hours at 35° C. Then the gold electrode was taken out, cleaned with distilled water for 10 minuets and dried at 35° C. for 2 hours to allow the formation of the nanopore by self-assembly. |

In addition, according to U.S. Pat. No. 6,582,583, the gold planer electrode was immersed in the solution for 24 hours at a room temperature. However, in an embodiment of the present invention, only one drop of the solution was applied onto the gold chip surface. After the application, the solution was immediately taken into incubation. The step of immersion in a sealed temperature for 24 hours at a room temperature was skipped.

Example 2

AFM Measurements

A clean bare gold chip with 50 nm thickness and 3 mm diameter was purchased (GeneFluidics, CA) for fabrication of the CD-SAM. Pretreatment of the chip before the fabrication is not necessary based on the AFM image of the bare gold surface. The same procedures and chemical mixtures as above were used to fabricate the gold CD-SAM chip in the clean room for the AFM measurements. The morphology of the three CD-SAMs against a bare gold electrode was characterized by using an instrument (Digital Instruments Dimension 3100 Atomic Force Microscope, Veeco Instruments, Santa Barbara, Calif.). The nanopore sizes were measured using TappingMode™ AFM with a silicon cantilever and tip with a 300 kHz resonance frequency and a 5-10 nm tip radius (Model TESP by VeecoProbes). The software used was Nano-Scope versions 5.30rl.

Figure 1B:
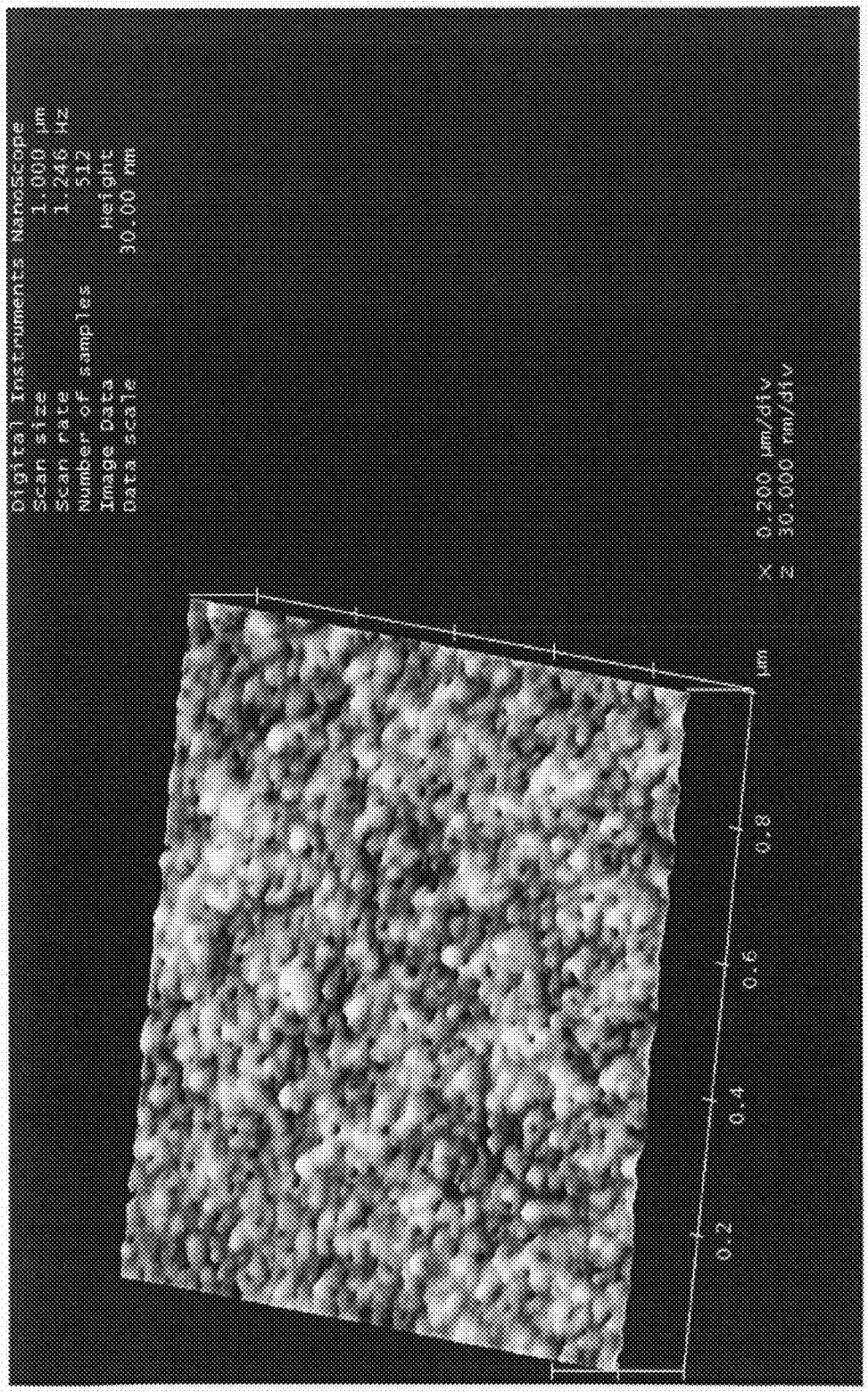
FIGS. 1B and 1C show 3D AFM (Atomic Force Microscopy) images for the same sensor as in FIG. 1A, respectively.
Figure 1C:
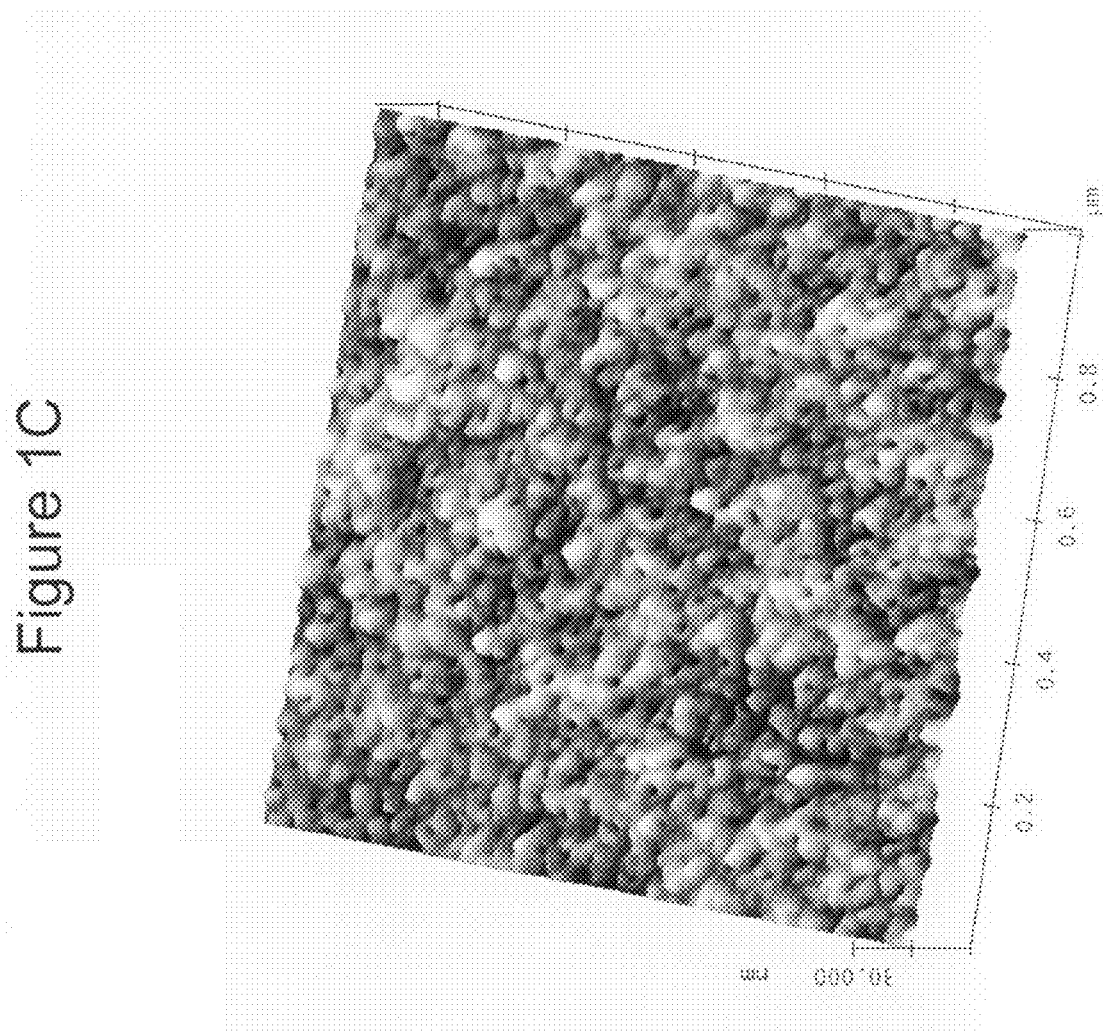
Figure 1E:
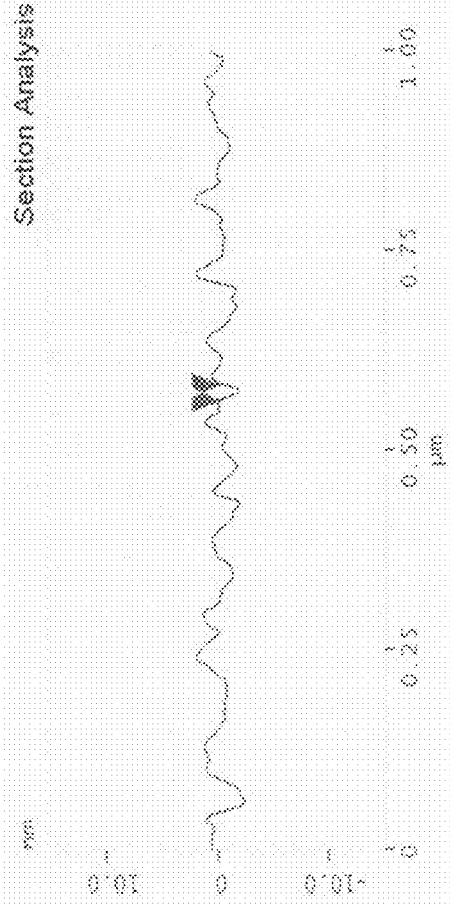
FIG. 1E shows the cross-sectional nanopore size measurement of the same sensor as in FIG. 1A.
Figure 2A:
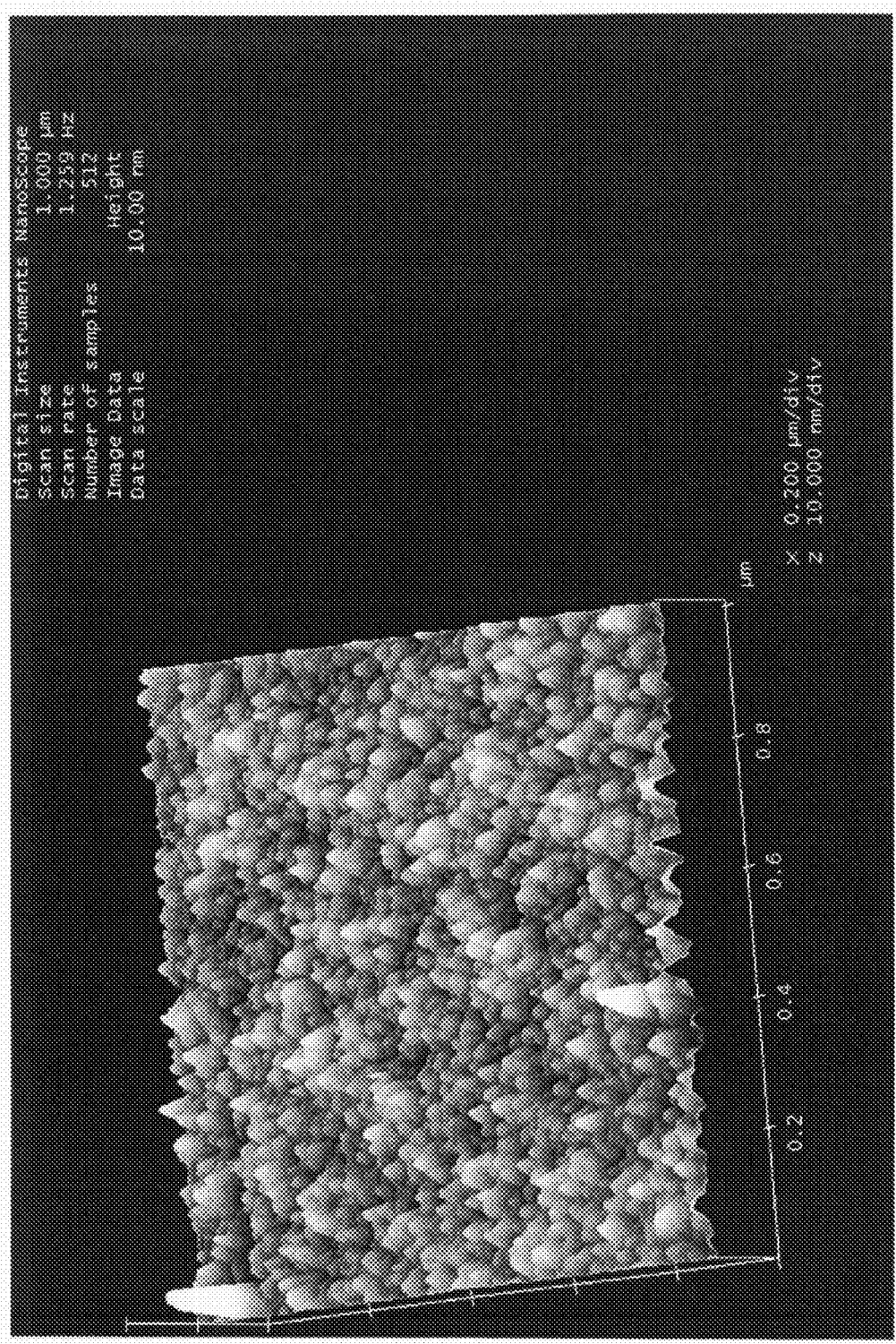
Figure 3A:
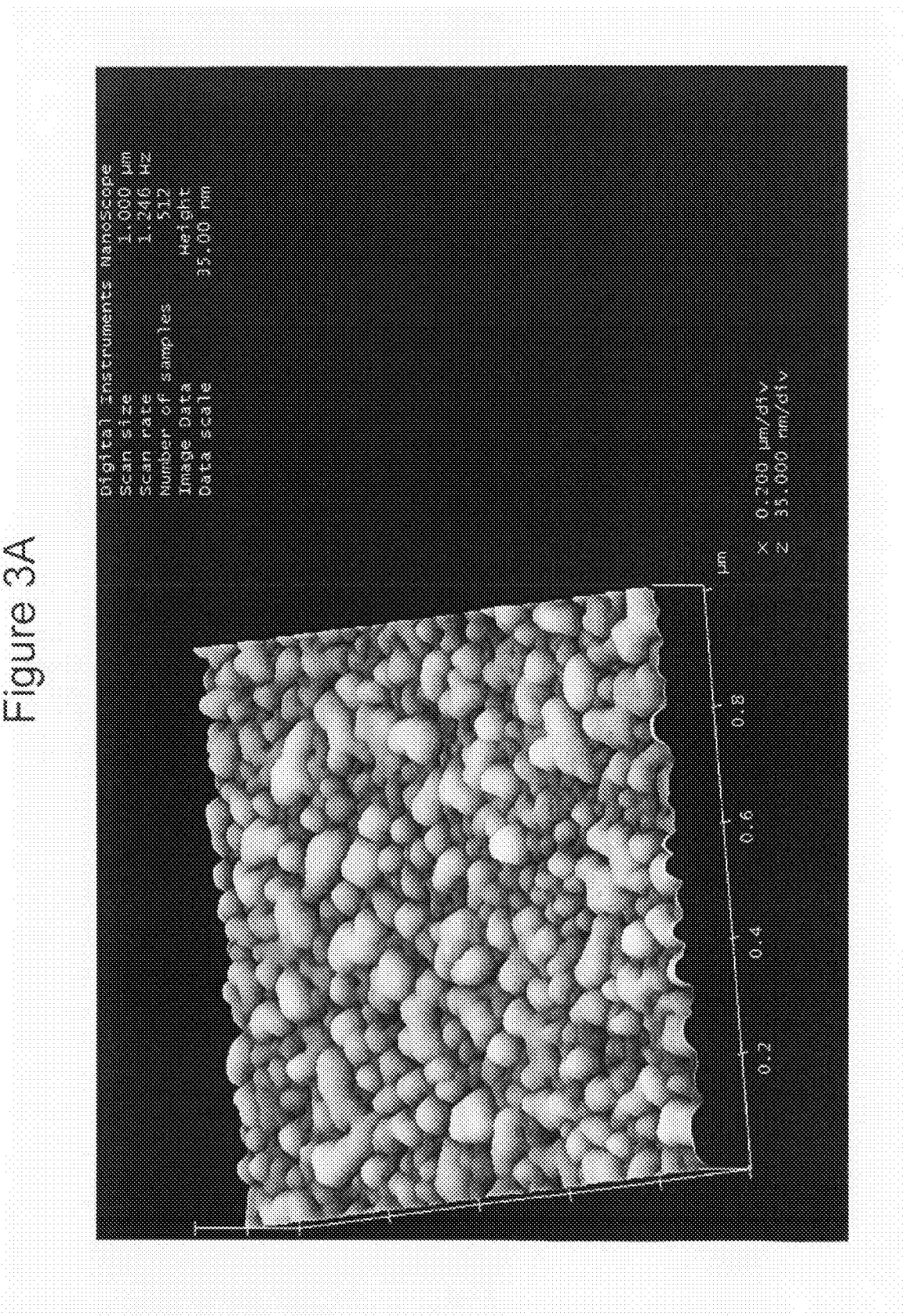
FIGS. 3A and 3B show AFM images of TCD/PEG/PVP CD copolymer gold electrode without nanopore structure, respectively.
Figure 3B:
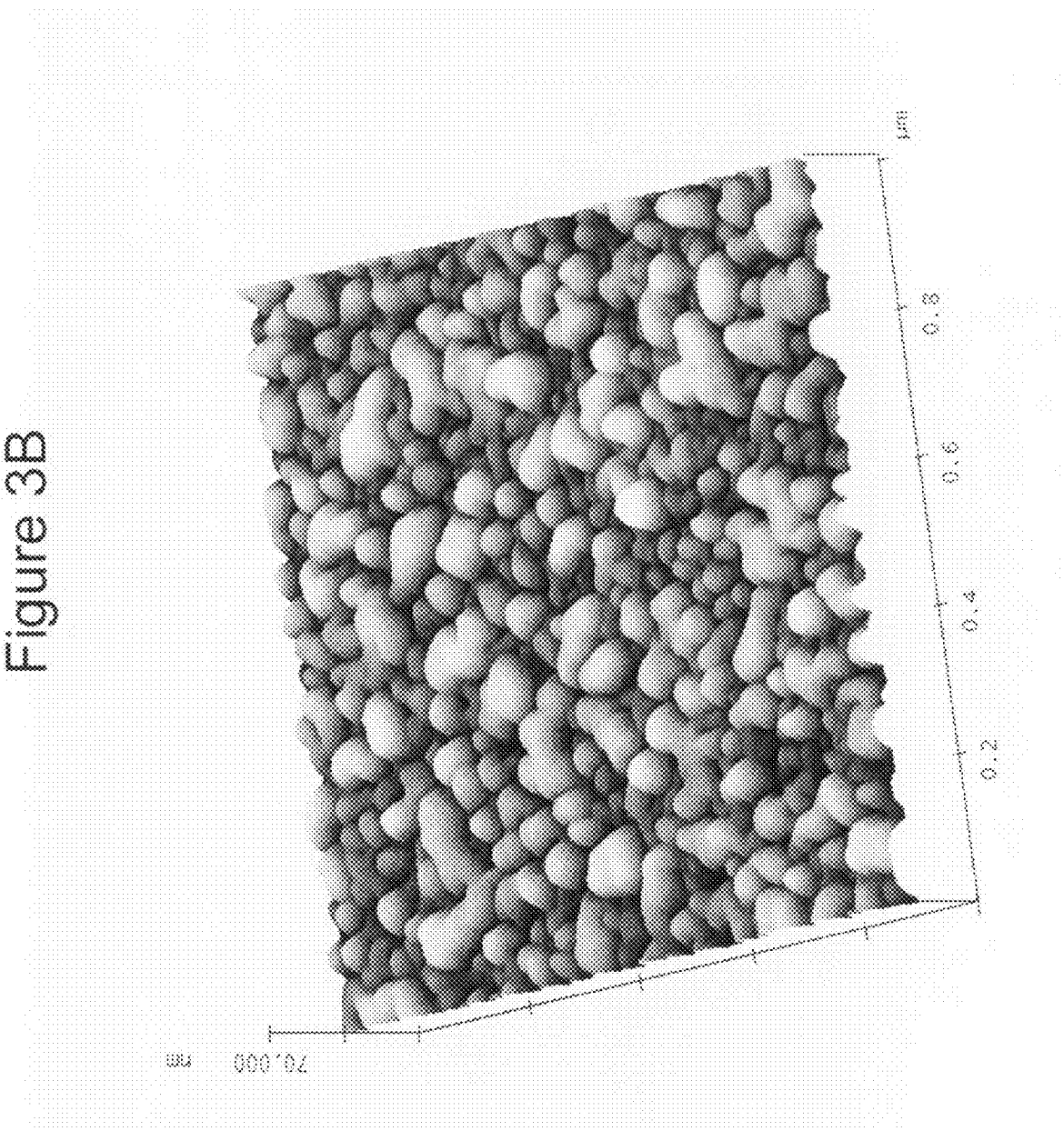

The first reported nanopore structured biomimetic CD-SAM was shown in FIG. 1A (two dimensional view, roughness measurement), FIGS. 1B and 1C (3D view), FIG. 1D (illustrative drawing) and FIG. 1E (pore size measurement). The images clearly revealed the smoothness of the SAM and the fact that the nanopores were evenly distributed and vertically oriented on the gold surface with the pore size from 10 nm to 20 nm, and the roughness of the SAM was 0.82 nm RMS. FIGS. 1D and 1E show the example of the pore size of 19.5 nm. FIGS. 2A and 2B are the 3D AFM images for a sensor with the same chemical composition and the receptor, but without nanopore structure. The nanopores were not observed. However, a "forest" of nano pillars (10-60 nm diameter) was observed covering the gold surface with a relative roughness of 16.65 nm in the z direction of the membrane, which was much rougher than the former sensor. FIGS. 3A and 3B are the AFM images for another type of sensors that were fabricated by the inventor, which had the same configuration as the sensor in FIG. 1A, except that triacetyl-β-CD(T-β-CD) instead of the receptored CD was used. The relative film roughness of the SAM membrane was 24.6 nm, which was too rough and the signature nanopore structure was not observed.

Example 3

Electrochemical Measurements

A voltammetric analyzer (model CV50W, Bioanalytical System (BAS), IN) was used for the measurements of currents. A Faraday low current cage (model C2, BAS) was used for protection of the electrode cell. For the pH effect study and for the glucose measurements, the scan rate was kept constant at 50 mv/s. All electrochemical measurements were done in an unstirred electrochemical cell at 20°C. All sample solutions were bubbled thoroughly with high purity $N_2$ for 10 minutes and maintained in a $N_2$ blanket. The 0.1 M, pH 7.0±0.1 buffer ((0.1 M KCl) solution was filtrated and degassed. The electrodes were equilibrated in a 10 mL, pH 7.0±0.1, 0.1 M buffer (0.1 M KCl) for 30-45 minutes by applying a potential at −400 mv until a steady-state current was observed before a sample can be measured.

The internal standard addition method was used to study the accuracy of glucose measurements using bovine serum albumin (BSA). The current for a 50 mg/dL glucose standard was measured in the 0.1 M phosphate buffer, pH 7 (0.1 M KCl) bovine serum albumin. Then 100 μL of 5 g/dL of glucose solution was added into the sera, and the current was measured. Four measurements were obtained after 4 consecutively additions of the same amount of glucose solution.

The electrochemical behavior of the sensors was characterized by using Cylic Voltammetry (CV) method. The factors affecting the currents were studied. The cyclic voltammograms of different electrodes with and without nanopore structured SAM membranes are compared in FIGS. 4A, 4B and 4C. In FIG. 4A, a well-defined irreversible reduction peak was observed for the nanopore sensor curves a and b, indicating that the nanopore structured CD-SAM was favorable for the DET between the active center of the imidazolyl in the cavity of mM-β-DMCD and the electrode. The decrease of the current shown in curve b indicates that the glucose molecules entered the CD cavity and mingled with the active receptor, hence suppressing the DET between the receptor and the electrode. FIG. 4B shows the electrochemical behavior for the T-β-CD's SAM electrode. The curves a and b have large envelop background currents. No DET peaks were observed for the bare gold electrode and for the T-β-CD electrode. FIG. 4C shows that there is no DET peak for mM-β-DMCD without nanopore structure, even it has the mimic His receptor, in the presence or absence of glucose. In FIG. 4C, the curves a and b overlap and the heavy envelop-like background currents exist, which was consistent with the morphology of the AFM image. FIG. 4A shows the electrocatalytic current and FIG. 4C does not have the current, even both sensors had the same biomimetic receptor, the differences being that the biosensor in FIG. 4A has the nanopore structure and the biosensor in FIG. 4C does not have the nanopore structure. This indicates that a lack of nanopore structure could hamper the DET even in the presence of an active receptor.

Example 4

Scan Rate Effects

Figure 9:
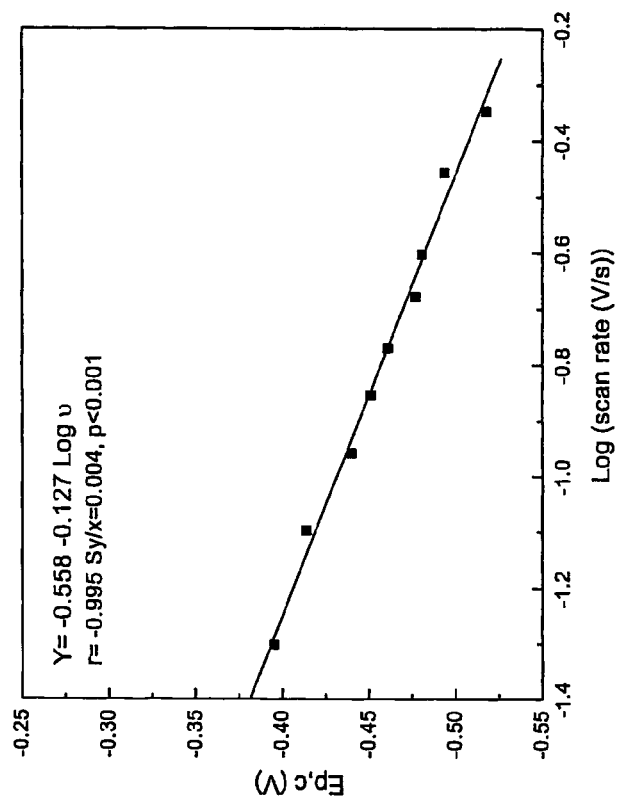
FIG. 9 shows the plot of $E_{p,c}$ (V) potential vs. long (v) scan rate according to the current obtained from the CV profiles in FIG. 8.
Figure 8:
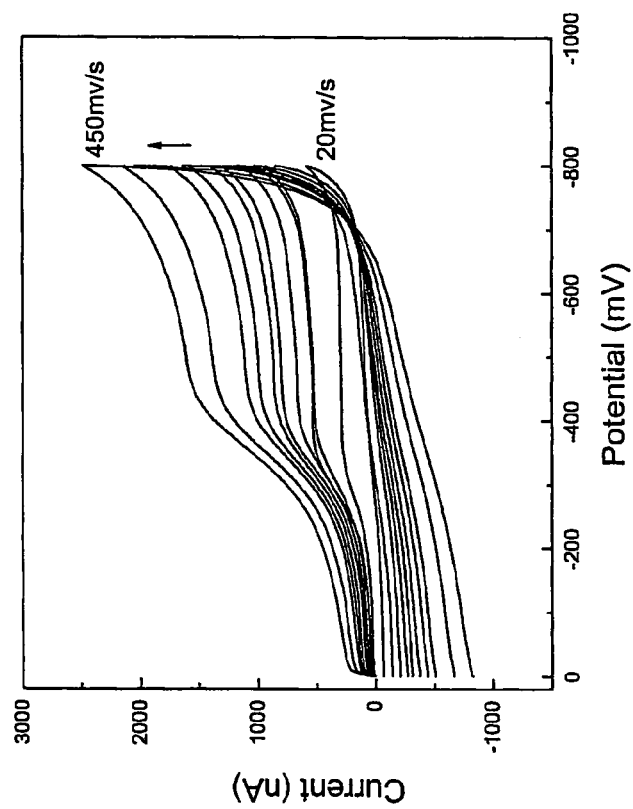
FIG. 8 shows the CV current profiles against the changing of scan rate at 20.0° C., pH 7.0±0.1, 0.1 M phosphate buffer (0.1 M KCl). The scan rate changed from 20 to 450 mv/s.

The scan rate effects on the electrochemical behavior of the nanopore CD sensor were studied and the voltammogram profiles were shown in FIG. 8. The reduction peak currents increased as the scan rate increased in the studied range from 20 mv/s up to 450 mv/s. The linearity study of the scan rate effect on the $E_{p,c}$ values is presented in FIG. 9. The nanopore structured CD sensor distinguished itself from other reported sensors that had reversible redox peaks (see references 3, 9, 25) and associated with the DET effect, which was the irreversible direct electron transfer. Possible explanations were that the effects of the nanopore structures were significant on DET. It played a significant role in promoting the DET. According to the commonly used E. Laviron's method, the DET rate constant for one nanopore structured CD-SAM sensor was calculated as 131±2.3/s based on three replicate measurements in neutral buffer, which had a 3.4-fold increased DET compared with 38.9±5.3/s for the rate constant for a gold nanoparticle-based glucose sensor using native glucose enzymes (see reference 9). The results also had a 3.11-fold faster rate than a GOD glucose sensor with single-walled carbon nanotubes (see reference 12).

Some of the advantages of the nanopored CD sensors of the present invention over the prior art native glucose enzyme sensors with gold nanoparticles or carbon nanotubes are: (1) the activation of the biosensor without the need of the presence of oxygen to detect glucose simplifies the procedures for commercialization; (2) the fabrication of truly reagentless, mediatorless nanopore CD sensors without the use of glucose enzyme avoided biofouling and denaturing from using native enzymes, which is an attractive characteristic for implantable devices or for usage in harmful environments.

Example 5 pH Effects

Figure 5:
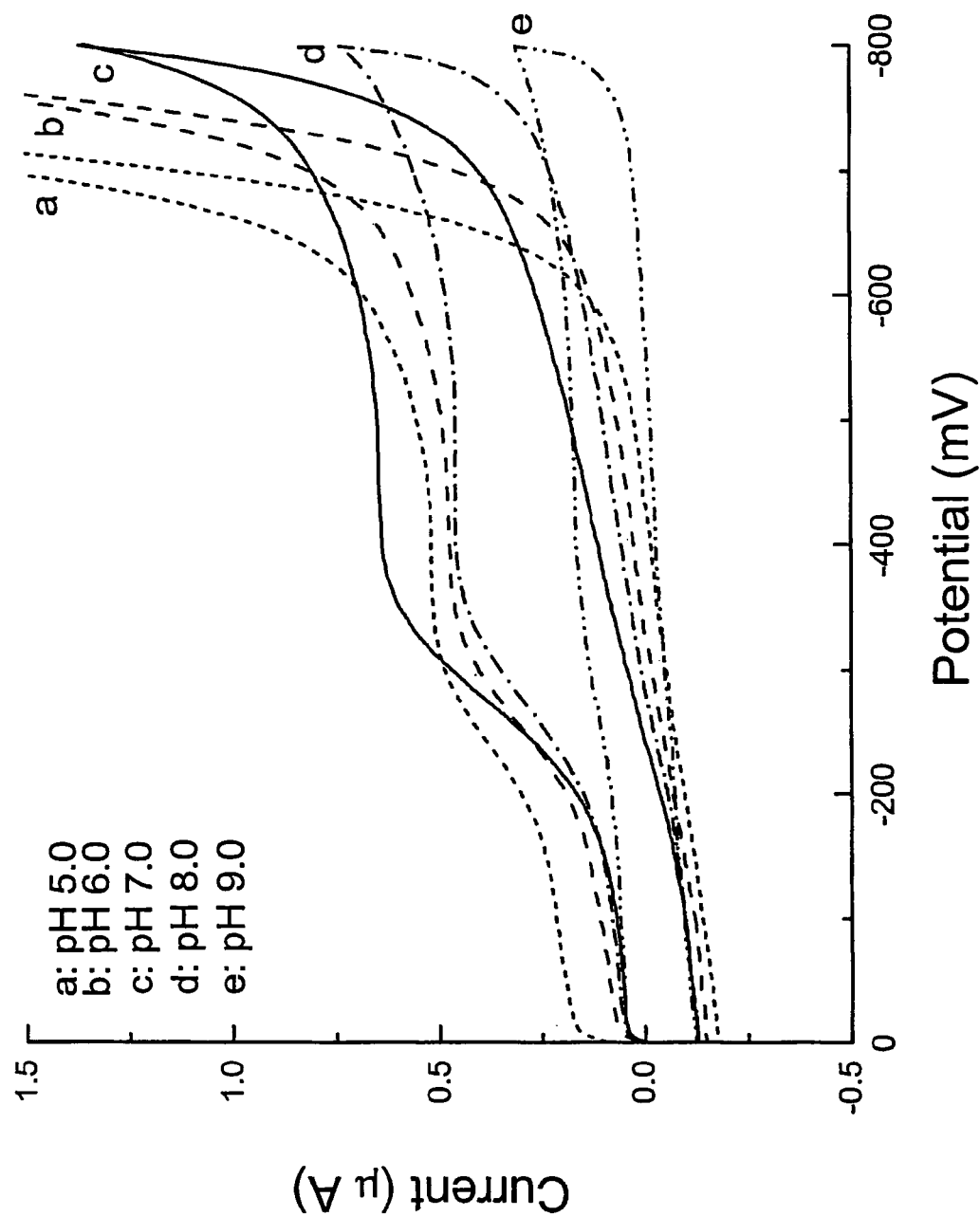
FIG. 5 shows CV profiles for the nanopored sensor with the mM-β-DMCD/PEG/PVP SAM membrane upon pH changes from 5.0 to 9.0 at same 0.1 M phosphate buffer with 0.1 M KCl.

The change of pH effects on the electrochemical behavior of the nanopored CD sensors was evaluated in 0.1 M phosphate buffer with varied pH from 5.0 to 9.0 without the presence of glucose at 20° C. as shown in FIG. 5. The highest peak intensity was observed at pH 7.0. The cathodic peak diminished at pH 9.0 indicated more negative ions from the solvent solution suppress the DET electron flow. The peak shifting slightly to a positive potential due to a decrease of pH was also observed. Therefore, the sensor is useful over a pH range of from about 5.0 to about 8.0.

Example 6

Nanopore Channeling Effect

Figure 6:
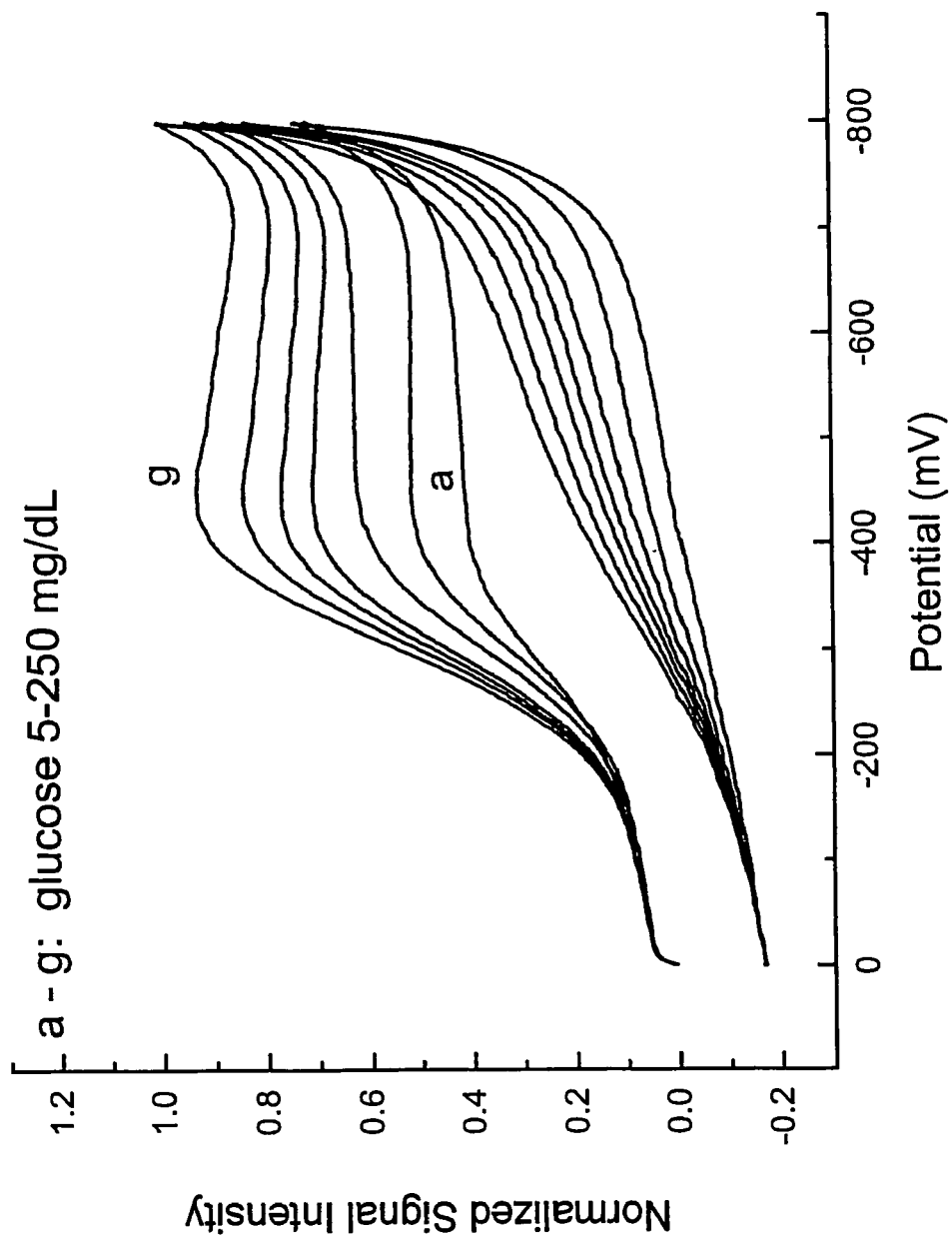
FIG. 6 shows the plots of normalized CV profiles of the same sensor as in FIG. 5 in the presence of various glucose concentrations from 5 mg/dL increased to 250 mg/dL labeled a to g, respectively.

Under optimal experimental conditions, curve c in FIG. 5 shows the optimal results, where DET occurred at a reduced potential around −390 mV. The cyclic voltammogram profiles are shown in FIG. 6 upon the addition of various standard glucose concentrations successively in the 10 mL pH 7.2 buffer solution. As shown in FIG. 4A, for curve b, the current decreases in the presence of glucose. The fact that electrocatalytic current increased proportionally with higher glucose concentration indicates that the channeling effect due to the nanopore structure had overcome the effect of glucose-receptor reaction resulting in the temporary suppression of the direct electron transfer. Recent published literature has revealed the fact that a decrease in current was observed as analyte concentration increased in gold nanoparticle sensors when native enzymes were used (see references 3, 9). This further provided evidence proving that when β-CD is lodged in the lumen of the α-hemolysin (HL) pore, it reduces the unitary conductance by about 70% (see reference 16), and the current reduces significantly when a voltage is applied onto the biological system in comparison with a system without an β-CD entering the α-HL pore.

Figure 10:
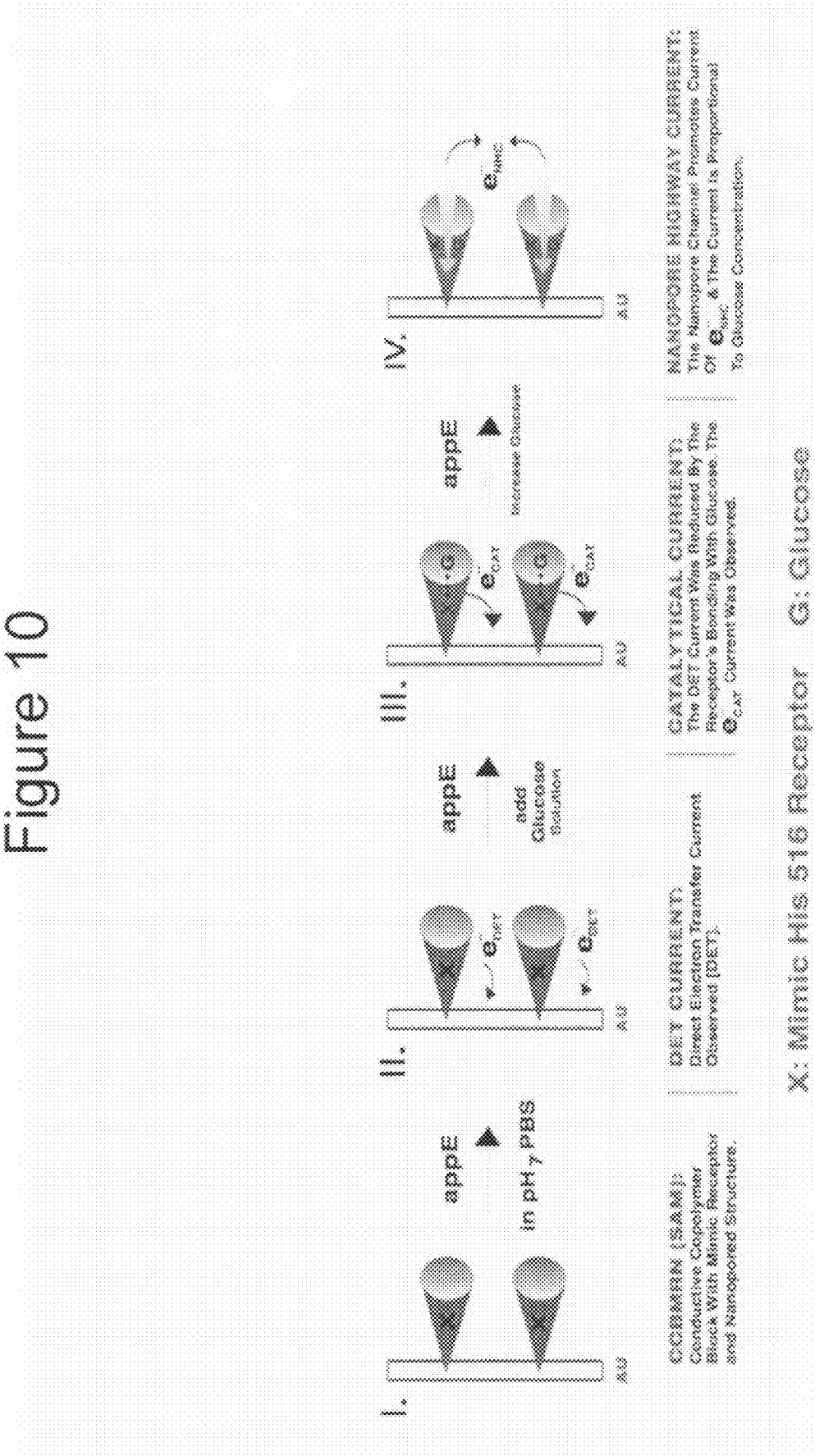
FIG. 10 illustrates the pathway for a nanopore sensor under an applied potential.

The experiments of the present invention not only confirm the nanopore sensor's electrochemical function, but also reveal a distinct phenomenon: at the beginning, a decrease of current is due to the association of the glucose molecules with the receptor site, and after that, an proportional increase of current is due to the nanopore channeling effect when the glucose concentration continues to increase. Detailed illustration of the pathway of the nanopore sensor is presented in FIG. 10.

Example 7

Accuracy and Biosensor Durability

For within-run precision, the relative mean standard deviation (RSD) was 1.5% from the triplicate runs obtained at each of 11 glucose concentration levels from 5 to 100 mg/dL. At the clinical decision level of 50 mg/dL, the RSD values were 1.1% and 1.4% (n=5) obtained at different days using the same nanopored CD sensor #1. At 20 mg/dL, which is a useful clinical decision level for diagnosing type I diabetic in newborns (see reference 23), the RSD value was 1.5%. For the inter-assay precision, the RSD values obtained from three CD sensors #1 with the same nanopored fabrication were 1.1%, 0.7% and 2% at 50.0 mg/dL glucose concentration with five replicates. The precision measurements of glucose at hypoglycemia range from the nanopored CD sensors have laid a foundation for accurate performance for future glucose monitoring devices. This improvement of the analytical performance has overcome the disadvantage of imprecise measurements common to self-monitoring blood glucose (SMBG) devices of the prior art at the low glucose range (see reference 23).

Three same types of nanopore structured CD sensor were fabricated on three 1.6 mm diameter gold electrodes and were used for the reproducibility study. The DET rate constants can be reproducibly obtained. The $K_s$ value was 136.7/s±19/s. The peak intensity deviation among the three sensors was 7.7%.

The internal standard addition method was used to study the accuracy of glucose measurements using bovine serum albumin (see reference 26). Four measurements were obtained after 4 consecutively additions of the 100 μL of 5 g/dL of glucose solution into the BSA. The results were compared against an internal standard. The mean accuracy was 98%±1% at 50 mg/dL concentration.

In prior art, native glucose enzyme sensors can suffer biofouling in which the glucose enzyme is easily dissociated from the electrode surface (see reference 9), and, therefore, it needs constant enzyme activity renewal in a solution. This problem does not occur with the nanopored CD sensor of the present invention. The CD sensor of the present invention never needs such a renewal process and still maintains a good performance. For example, the intensity of the same CD sensor only decrease by 16% after 116 measurements lasted for 42 days. Plus, the sensor does not need to be kept at 4° C. for storage as required by native enzyme sensors (see reference 3). Therefore, the nanopore CD sensors of the present invention have offered advantageous features that are simple and robust for direct glucose measurements without using glucose enzymes or mediators.

Example 8

Sensitivity of an Arrayed-Nanopored Biosensor

Figure 7:
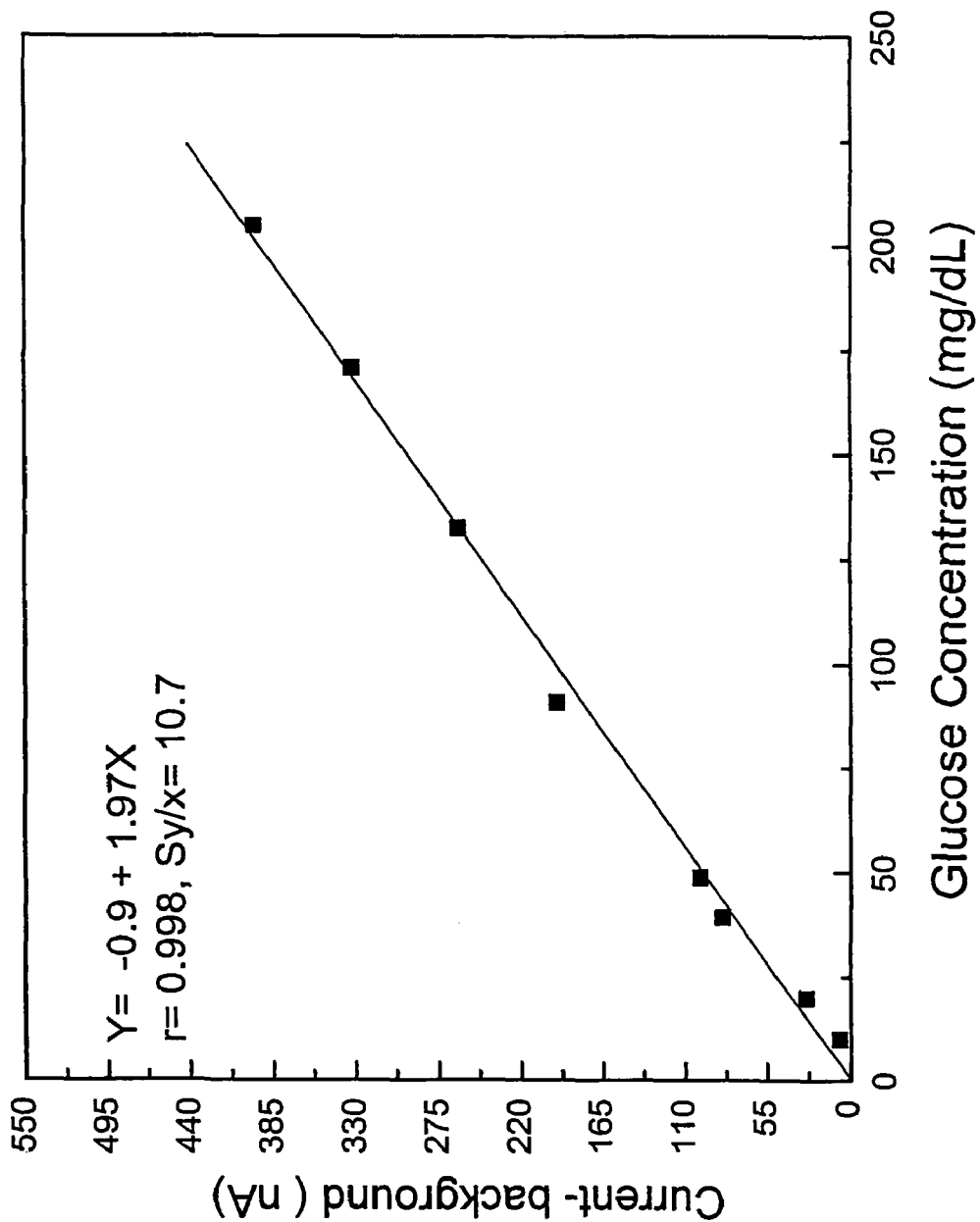
FIG. 7 shows the plot of current vs. glucose concentration by using a sensor in FIG. 6.

As shown in FIG. 6, the well-defined electrocatalytic response curves for glucose are presented by utilizing the arrayed-nanopore SAM with an artificial electrocatalytical functioning receptor. A plot of current vs. glucose concentration illustrates the linearity of the nanopored CD sensor's analytical performance presented in FIG. 7. The least-squares statistical results obtained from current vs. glucose concentrations produced an equation Y(nA)=−0.9(nA)+1.97×(nA/mgdL$^{-1}$) with a linear range up to 205 mg/dL with the Correlation Coefficient of r=0.998, $S_{y/x}$=10.7 nA. The sensitivity of the sensor is 3.55 nA/μmol/L in 2.01 mm$^2$ electrode surface, which is 118-fold sensitive than that of the prior arts (Chen, 2003, see reference 17), and 33.040-fold enhanced the sensitivity compared with Liu's glucose electrochemical cyclodextrin polymer sensor (Liu et al. 1998, see reference 27). The calculated Limit of Detection (LOD) for glucose using the current invented arrayed-nanopored sensor is 3.1 nM/mm$^2$, which are 1.9×10$^3$ molecules of glucose/nm$^2$.

Example 9

Performance at Hypoglycemia Range

This glucose biosensor of the present invention demonstrates the full usages of monitoring glucose at critical clinical decision concentration ranges (FIG. 7) from hypoglycemia to hyperglycemia ranges. The least-squares statistic result in the hypoglycemia range from 5 to 50 mg/dL produced an equation of y=−0.008 μA+0.007×(μA/mg/dL) with Correlation Coefficient of 0.999 (n=30 with three replicates at each of 10 concentration levels), and has the $S_{y/x}$ value of 0.006 μA, corresponding to a relative standard deviation of 1.6% at the 50 mg/dL clinical decision level for type I diabetic hypoglycemia.

Example 10

Glassy Carbon Electrode

In addition to gold, glassy carbon can be used for construction of the biosensor of the present invention. The DET effect was observed and the irreversible peaks were also obtained.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

REFERENCES

The following references are hereby incorporated by reference.

1. L Goorton, A. Lindgren, T. Larsson, F. D. Munteanu, T. Ruzgas and L Gazaryan, *Direct eletrontransfer between heme-containing enzymes and electrodes as basis for third generation biosensors*, Anal. Chim, Acta 400, 91, (1999).
2. S. J. Updike, G. P. Hicks, Nature 214, 986, (1967).
3. Z. Dai, F. Yan, J. Chen and H. Ju, *Reagentless amperometric immunosensors based on direct electrochemistry of horseradish peroxidase for determination of carcinoma antigen-125*, Anal. Chem. 75, 5429, (2003).
4. Y. Tian, L. Mao, T. Okajima, T. Oshaka, Anal. Chem 74, 2428-2434, 2002.
5. T. Ruzgas, E. Csöregi, J. Emneus, L Gorton, and G. Marko-varga. *Anal. Chim. Acta,* 330, 123, (1996).
6. S. Y. lu, C. E. Li, D. D. Zhang, Y, Zhang, Z. H. Mo, Q. Cai and A. R. Zhu. *Electron transfer on an electrode of glucose oxidase immobilized in polyaniline, J. Electroanal. Chem.* 364, 31, (1994).
7. P. De Taxis Du Poet, S. Miyamoto, T. Murakami, J. Kimura and I. Karube. *Direct electron transfer with glucose oxidase immobilized in an electropolymerized poly(N-methylpyttole) film on a gold microelectrode, Anal. Chim. Acta,* 2365, 255, (1990).
8. J. Wang, L. Liu, L. Chen and F. Lu, *Highly selective membrane-free, mediator-free glucose biosensor,* Anal Chem 66, 3600, (1994).
9. S. Liu and H. Ju, *Reagentless glucose biosensor based on direct electron transfer of glucose oxidase immobilized on colloidal gold modified carbon paste electrode, Biosensors and Bioelectronics,* 19(3), 177, (2003).
10. J. Zhao, R. W. Henkens, J. Stonehuemer, J. P. O'Daly and A. L. Crumbliss. *Direct electron transfer at horseradish peroxidase-colloidal gold modified electrodes. J. Electroanal. Chem.* 327, 109, (1992).
11. J. Wang et al, *Carbon-nanotube based electrochemical biosensors: a review, Electroanalysis* 17(1), 7, (2004).
12. J. Wang, *Nanomaterial-based electrochemical biosensors, Analyst,* 130, 421, (2005).
13. A. Vaseashta and J. Irudayaraj, *Nanostructured and nanoscale devices and sensors, J. Optoelectronics and advanced materials* 7(1), 35, (2005).
14. B. Ei-Zahab, H. Jia and P. Wang, *Enabling multienzyme biocatalysis using nanoporous materials, Biotechnology and Bioengineering,* 87(2), 178, (2004).
15. X. Zhao, B. Xiao, A. Fletcher, K. M. Thomas, D. Bradshaw, and M. J. Rosseinsky, *Hysteretic adsorption and desorption of hydrogen by nanoporous metal-organic framework, Science,* 306, 1012, (2005).
16. L-Q Gu, S. Chelay and H. Bayley, *Electroosmotic enhancement of the binding of a neutral molecule to a transmembrane pore, Proceed. National Acad. Assoc.* 100(26), 15498, (2003).
17. E. T. Chen. *Amperometric biomimetic enzyme sensors based on modified cyclodextrin as electrocatalysts, U.S. Pat. No. 6,582,583 issued on Jun. 24, 2003.*
18. L. Gu, S. Cheley and H. Bayley, *Prolonged residence time of a noncovalent molecular adapter, β-cycledexrin, within the lumen of mutant α-hemolysin pores, J. General Physiology,* 118(5), 481, (2001).

19. D. Branton and J. Golovchenko, *Biochemical sensors: adapting to nanoscale events*, Nature, 398, 660 (1999).
20. H. Bayley, L. Jayasinghe, *Functional engineered channels and pores*, Mol. Membr. Biol, 21(4), 209, (2004).
21. H. Bayley and P. S. Cremer, *Stochastic sensors inspired by biology*, Nature 413, 226, (2001).
22. P. A. Gale, *A "Holey" superamolecular approach to the detection of enzyme activity*, ChemBiochem, 4(12), 1299, (2003).
23. E. T. Chen, J. Nichols, S. H. Duh and G. Hortin. *Evaluation of performance of self-monitoring glucose meters*, Diabetes Technology & Therapeutics 5(5), 749, (2003).
24. R. Prakhakar, P. E. M. Siegbahn and B. F. Minaev, *A theoretical study of the deoxygen activation by glucose oxidase and copper amine oxidase*, Biochemica & Biophysics Acta, 1647, 173, (2003).
25. S. Liu, Z. Dai, H. Chen and H. Ju, *Immobilization of hemoglobin on zirconium dioxide nanoparticles for preparation of a novel hydrogen peroxide biosensor*, Biosensors and Bioelectronics, 19(9), 963, (2004).
26. H. B. Dick, R. J. Olson, A. J. Augustin, O. Schwenn, G. Magdowski and N. Pfeiffer, *Vacuoles in the acrysof intraocular lens as factor of the presence of serum in aqueous humor*, Ophthalmic Res 23, 61, (2001).
27. H, Liu et al. "Amperometrcic biosensor sensitive to glucose and lactose based on co-immobilization of ferrocene, glucose oxidase, beta-galactosidase and mutarotase in beta-cyclodextrin polymer", Analytica Chimica Acta 1998, 358, 137-144.
28. Y. Kondo et al. "Thickness induced structure phase transition of gold nanofilm" Phys. Rev. 1999, 82, 751-754.

The invention claimed is:

1. A method of measuring the concentration of a material in a sample, comprising the steps of:
   obtaining a sample which can be detected;
   contacting the sample with a sensor, wherein the sensor comprises an electrode; and one or more nanopore sensors comprising a cyclodextrin in the form of a nanopore, electrocatalytically active and affixed to said electrode, wherein the one or more nanopore sensors are oriented vertically on the electrode and wherein direct electron transfer (DET) occurs between the one or more nanopore(s) and the electrode when a voltage is applied to the electrode, and wherein the cyclodextrin forms a uniform arrayed-nanopore membrane in a range of about 10-20 nm pore size and with its pin-hole free, and wherein the sensor has a nanopore channeling effect;
   measuring the current between the one or more nanopore sensors and the electrode; and
   correlating the concentration of the material in the sample with the intensity of the current being measured, and wherein said one or more, nanopore sensors comprising said cyclodextrin further comprises at least one imidazole group which has a conformation which mimics histidine residue (His-516) of glucose oxidase.

2. The method according to claim 1, wherein the sample comprises a bodily fluid.

3. The method according to claim 1, wherein the material to be measured comprises glucose.

4. The method according to claim 3, wherein said cyclodextrin is cross-linked with polyethylene glycol (PEG) and poly-4-vinylpyridine (PVP) to form a self-assembly membrane.

5. A method of constructing a sensor comprising the steps of:
   providing an electrode;
   contacting the electrode with a solution, wherein the solution comprises a cyclodextrin chemically modified to mimic an active site of an enzyme to be electrocatalytically active; affixing the modified cyclodextrin to the electrode where the cyclodextrin forms one or more nanopore sensors, and wherein the nanopore sensors are oriented vertically on the electrode; and wherein direct electron transfer (DET) occurs between the nanopore(s) and the electrode when a voltage is applied to the electrode, and wherein said cyclodextrin of the one or more nanopore sensors comprises at least one imidazole group which has a conformation which mimics histidine residue (His-516) of glucose oxidase.

6. The method according to claim 5, wherein the solution comprises polyethylene glycol (PEG) and poly-4-vinylpyridine (PVP).

7. A method of measuring the concentration of a glucose in a sample, comprising the steps of:
   obtaining a sample which can be detected;
   contacting the sample with a sensor, wherein the sensor comprises an electrode; and one or more nanopore sensors comprising a cyclodextrin in the form of a nanopore, electrocatalytically active and affixed to said electrode, wherein the one or more nanopore sensors are oriented vertically on the electrode and wherein direct electron transfer (DET) occurs between the one or more nanopore sensors and the electrode when a voltage is applied to the electrode;
   the one or more nanopore sensors also having a cyclodextrin further comprising at least one imidazole group which has a conformation which mimics histidine residue (His-516) of glucose oxidase;
   the cyclodextrin of the one or more nanopore sensors is cross-linked with polyethylene glycol (PEG) and poly-4-vinylpyridine (PVP) to form a self-assembling membrane;
   measuring the current between the one or more nanopore sensors and the electrode; and
   correlating the concentration of the glucose in the sample with the intensity of the current being measured.

8. A sensor comprising:
   an electrode; and
   one or more nanopore sensors comprising a cyclodextrin in the form of a nanopore, electrocatalytically active and affixed to said electrode, wherein the one or more nanopore sensors are oriented vertically on the electrode and wherein direct electron transfer (DET) occurs between the one or more nanopore(s) and the electrode when a voltage is applied to the electrode, and wherein the cyclodextrin forms a uniform arrayed-nanopore membrane in a range of about 10-20 nm pore size and with its pin-hole free, and wherein the sensor has a nanopore channeling effect, wherein said cyclodextrin comprises at least one imidazole group and wherein the at least one imidazole group is in a conformation which mimics the histidine residue (His-516) of glucose oxidase.

9. The sensor according to claim 8, wherein the electrode comprises gold or glassy carbon.

10. The sensor according to claim 8, said sensor being mediator free.

11. The sensor according to claim 8, wherein said sensor is free of glucose oxidase (GOx) enzyme.

12. The sensor according to claim 8, said sensor being useful over a pH range of from about 5 to about 8.

13. The sensor according to claim 8, being bioselective for glucose.

14. The sensor according to claim 8, said sensor having a direct electron transfer (DET) rate constant of 131±2.3/second.

15. The sensor according to claim 8, said sensor having a limit of detection (LOD) of 3.1 nmol/L/mm$^2$.

16. The sensor according to claim 8, wherein the relative standard deviation of the measurements of the sensor is about 1.5%.

17. The sensor according to claim 8, wherein said cyclodextrin is cross-linked with a polymer.

18. The sensor according to claim 17, wherein said polymer comprises polyethylene glycol (PEG).

19. The sensor according to claim 17, wherein said polymer comprises poly-4-vinylpyridine (PVP).

20. The sensor according to claim 17, wherein said cross-linking is through self-assembly.

21. The nanopore sensor of claim 8, wherein the cyclodextrin pores have an internal pore size of about 10-20 nm, a pore height of about 8 nm, and the roughness of the membrane is about 0.55 nm (RMS) when measured by section analysis.

22. The method according to claim 21, wherein the cyclodextrin pores are uniformly self-assembled, and free from pin-hole.

23. A sensor for detecting glucose comprising:
an electrode; and
one or more nanopore sensors comprising a cyclodextrin in the form of a nanopore, electrocatalytically active and affixed to said electrode, wherein the one or more nanopore sensors are oriented vertically on the electrode and wherein direct electron transfer (DET) occurs between the one or more nanopore sensors and the electrode when a voltage is applied to the electrode,
the one or more nanopore sensors also having a cyclodextrin further comprising at least one imidazole group which has a conformation which mimics histidine residue (His-516) of glucose oxidase; and
the cyclodextrin of the one or more nanopore sensors is cross-linked with polyethylene glycol (PEG) and poly-4-vinylpyridine (PVP) to form a self-assembling membrane.

24. The sensor according to claim 23, wherein the electrode comprises gold.

* * * * *